United States Patent
Sedelmeier et al.

(10) Patent No.: US 7,208,623 B2
(45) Date of Patent: Apr. 24, 2007

(54) PROCESS FOR THE MANUFACTURE OF HMG-COA REDUCTASE INHIBITORY MEVALONIC ACID DERIVATIVES

(75) Inventors: Gottfried Sedelmeier, Schallstadt (DE); Christian Mathes, Offenburg (DE)

(73) Assignee: Novartis AG, Basel (CH)

( * ) Notice: Subject to any disclaimer, the term of this patent is extended or adjusted under 35 U.S.C. 154(b) by 427 days.

(21) Appl. No.: 10/504,655

(22) PCT Filed: Feb. 20, 2003

(86) PCT No.: PCT/EP03/01738

§ 371 (c)(1),
(2), (4) Date: Aug. 13, 2004

(87) PCT Pub. No.: WO03/070717

PCT Pub. Date: Aug. 28, 2003

(65) Prior Publication Data

US 2005/0159480 A1   Jul. 21, 2005

(30) Foreign Application Priority Data

Feb. 21, 2002   (GB) ............... 0204129.1

(51) Int. Cl.
C07C 59/00   (2006.01)
(52) U.S. Cl. .................................. 562/577
(58) Field of Classification Search ......... 562/577, 562/579, 580, 598, 600
See application file for complete search history.

(56) References Cited

U.S. PATENT DOCUMENTS

| | | | |
|---|---|---|---|
| 4,851,427 A | 7/1989 | Wareing | 514/422 |
| 5,273,995 A | 12/1993 | Roth | 514/422 |
| 5,399,722 A | 3/1995 | Beck et al. | 549/375 |
| 5,763,688 A | 6/1998 | Ikariya et al. | 568/814 |
| 6,184,381 B1 | 2/2001 | Ikariya et al. | 546/136 |
| 6,211,412 B1 | 4/2001 | Georg et al. | 568/309 |
| 2002/0156289 A1* | 10/2002 | Georg et al. | 548/203 |

FOREIGN PATENT DOCUMENTS

| | | |
|---|---|---|
| EP | 0 304 063 | 2/1989 |
| EP | 0 916 637 | 5/1999 |
| EP | 1 134 226 | 9/2001 |
| EP | 1 136 475 | 9/2001 |
| WO | WO 01/92223 | 12/2001 |
| WO | WO 02/008169 | 1/2002 |
| WO | WO 03/070717 | 8/2003 |

OTHER PUBLICATIONS

Tetrahedron Letters, 45(30), 5845-5847; 2004.*
Matsumura, Hashiguchi, Ikariya and Noyori, "Asymmetric Transfer Hydrogenation of α,β-Acetylenic Ketones", *J Am Chem Soc*, vol. 119, No. 37, pp. 8738-8739 (1997).
Noyori and Ohkuma, "Asymmetric Catalysis by Architectural and Functional Molecular Engineering: Practical Chemo- and Stereoselective Hydrogenation of Ketones", *Angew Chem Int Ed*, vol. 40, No. 1, pp. 40-73 (2001).
Noyori, Yamakawa and Hashiguchi, "Metal-Ligand Bifunctional Catalysis: A Nonclassical Mechanism for Asymmetric Hydrogen Transfer Between Alcohols and Carbonyl Compounds", *J Org Chem*, vol. 66, No. 24, pp. 7931-7944 (2001).
Ohkuma et al., "Selective Hydrogenation of Benzophenones to Benzhydrols. Asymmetric Synthesis of Unsymmetrical Diarylmethanols", *Org Lett*, vol. 2, No. 5, pp. 659-662 (2000).
Ohkuma et al., "Asymmetric Hydrogenation of Alkenyl, Cyclopropyl, and Aryl Ketones. RuCl$_2$(xylbinap)(1,2-diamine) as a Precatalyst Exhibiting a Wide Scope", *J Am Chem Soc*, vol. 120, No. 51, pp. 13529-13530 (1998).
Repic, Prasad and Lee, "The Story of Lescol: From Research to Production", *Org Process Res Dev*, vol. 5, No. 5, pp. 519-527 (2001).
Suzuki et al., "First Systematic Chiral Syntheses of Two Pairs of Enantiomers with 3,5-Dihydroxyheptenoic Acid Chain, Associated with a Potent Synthetic Statin NK-104", *Bioorg Med Chem Lett*, vol. 9, No. 20, pp. 2977-2982 (1999).

* cited by examiner

*Primary Examiner*—Thurman K. Page
*Assistant Examiner*—Karl Puttlitz
(74) *Attorney, Agent, or Firm*—John W. Kung

(57) ABSTRACT

The invention relates to a process for the manufacture of a compound of formula: (Formula I); or a salt, especially a pharmaceutically acceptable salt with a base, thereof or a lactone thereof wherein the element (a) represents —CH$_2$—CH$_2$— or —CH=CH— and R represents a cyclic radical.

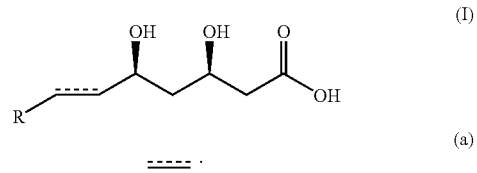

3 Claims, No Drawings

PROCESS FOR THE MANUFACTURE OF HMG-COA REDUCTASE INHIBITORY MEVALONIC ACID DERIVATIVES

The invention relates to a process for the manufacture of HMG-CoA reductase inhibitors, to process steps, to novel intermediates and to novel catalysts.

HMG-CoA reductase inhibitors (also called β-hydroxy-β-methylglutaryl-co-enzyme-A reductase inhibitors and also called statins) are understood to be those active agents which may be preferably used to lower the lipid levels including cholesterol in blood and can be used e.g. for the prevention or treatment of hyperlipidemia and artheriosclerosis.

The class of HMG-CO-A reductase inhibitors comprises compounds having differing structural features. For example, mention may be made of the compounds which are selected from the group consisting of atorvastatin, cerivastatin, fluvastatin, lovastatin, pitavastatin (formerly itavastatin), pravastatin, rosuvastatin, and simvastatin, or, in each case, a pharmaceutically acceptable salt thereof.

Preferred HMG-Co-A reductase inhibitors are those agents which have been marketed, most preferred is fluvastatin, atorvastatin, pitavastatin, especially the Calcium salt thereof, or simvastatin or a pharmaceutically acceptable salt thereof.

Atorvastatin of formula

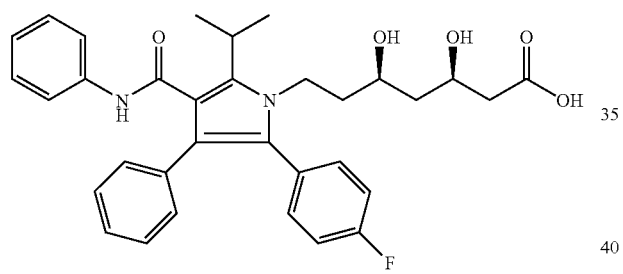

is disclosed and claimed in U.S. Pat. No. 5,273,995.

Cerivastatin of formula

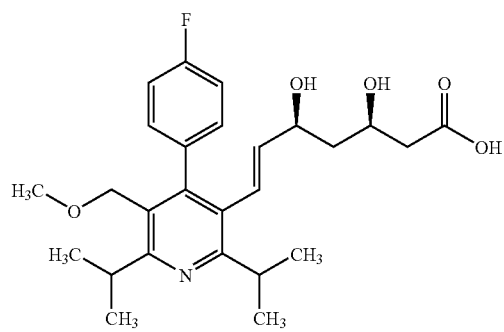

is disclosed and claimed in U.S. Pat. No. 5,177,080.

(+)-(5S,3R)-Form of fluvastatin of formula

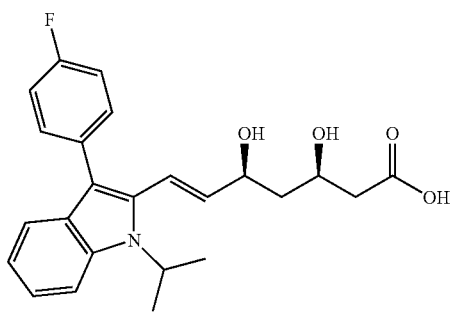

is disclosed and claimed in U.S. Pat. No. 5,345,772.

Lovastatin of formula

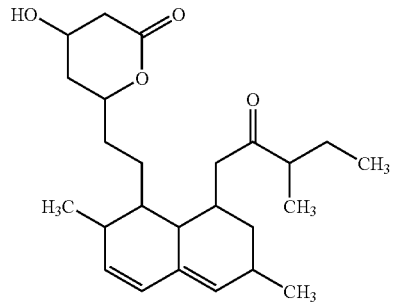

is disclosed and claimed in U.S. Pat. No. 4,231,938.

Pitavastatin of formula

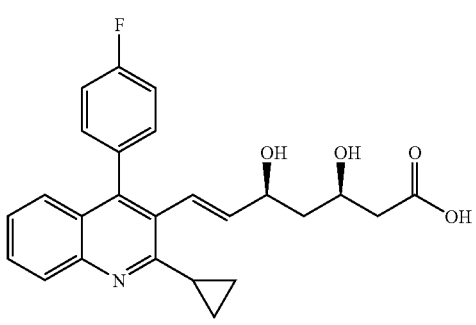

is disclosed and claimed in U.S. Pat. No. 5,856,336.

Pravastatin of formula

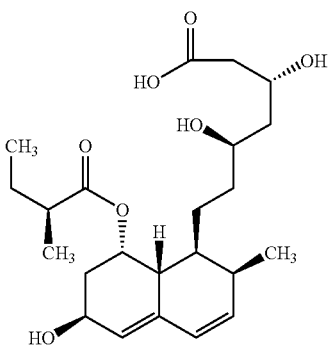

is disclosed and claimed in U.S. Pat. No. 4,410,629.

Rosuvastatin of formula

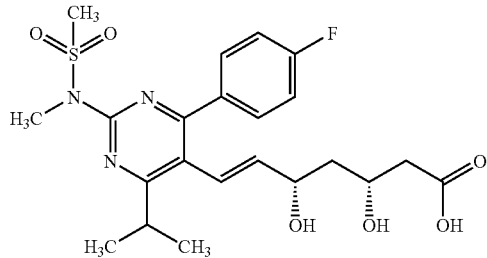

is disclosed and claimed in U.S. Pat. No. 5,260,440.

Simvastatin of formula

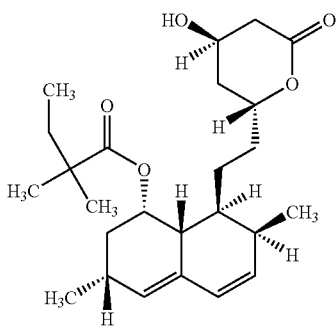

is disclosed and claimed in U.S. Pat. No. 4,444,784.

The structure of the active agents identified hereinbefore or hereinafter by generic or tradenames may be taken from the actual edition of the standard compendium "The Merck Index" or from databases, e.g. Patents International or LifeCycle Patents International, respectively, (e.g. IMS World Publications). The corresponding content thereof is hereby incorporated by reference. Any person skilled in the art is fully enabled to identify the active agents and, based on these references, and is likewise enabled to manufacture and test the pharmaceutical indications and properties in standard test models, both in vitro and in vivo.

Acidic representatives of HMG-Co-A reductase inhibitors have been launched are being developed as salts, for example, fluvastatin as sodium salt and pitavastatin as calcium salt.

The corresponding active ingredients or a pharmaceutically acceptable salts thereof may also be used in form of a solvate, such as a hydrate or including other solvents, used for. crystallization.

Essentially, statins comprise a cyclic core element and a side chain element of formula

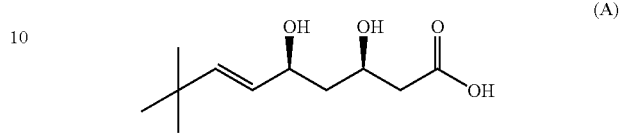

(A)

(a 3,5-dihydroxy-hept-6-enoic acid moiety) that might form a corresponding lactone partial structure of formula

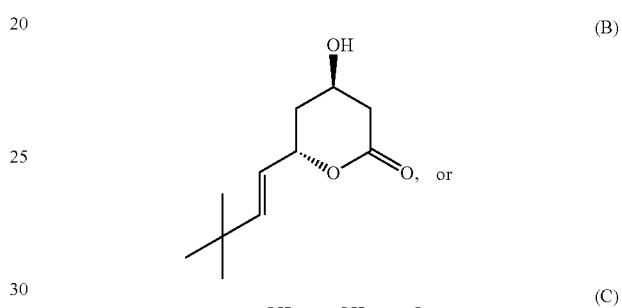

(B)

, or (C)

or (a 3,5-dihydroxy-heptanoic acid derivative) that might form a corresponding lactone partial structure of formula

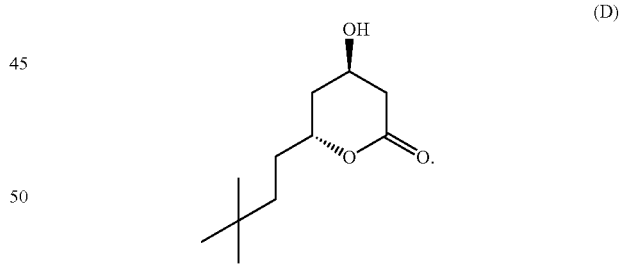

(D)

In said side chain elements (A) or (C), respectively, the 3,5-syn diol structure and the R-configuration at C-3 are essential features, as corresponding statins with this specific element exhibit the highest biological activity.

The objective of the present invention is to provide an enantioselective synthesis of compounds of formula (I) resulting in high yields and moreover guaranteeing a minimization of the ecological pollution of the environment, being economically attractive, e.g. by using less reaction steps in the reaction sequence for the manufacture of compounds of formula I, and leading to largely enantiomerically pure target products and to products of high crystallisability. Furthermore, another objective of the present invention is to provide a process that can be carried out in a larger scale and can thus be used for a corresponding production process. Furthermore, there is a need to avoid any separation of any stereoisomers.

Surprisingly, the process of the present invention clearly meets the above objectives. The process relates to an enantioselective synthesis by using essentially the so-called transfer hydrogenation approach. For example, an enantiomer excess (ee) of a compound of formula (I) of ≧95%, preferably ≧98% and most preferably ≧99% can be achieved.

The invention relates to a process for the manufacture of a HMG-COA reductase inhibitory mevalonic acid derivative of formula (I a)

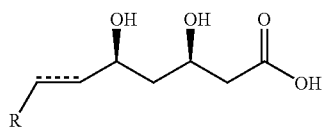
(I)

or a salt, especially a pharmaceutically acceptable salt with a base, thereof or a lactone thereof wherein the element

----- represents —CH₂—CH₂— or —CH=CH— and R represents a cyclic residue.

A salt of a compound of formula (I) is, for example, a salt with a base, preferably a corresponding pharmaceutically acceptable salt thereof.

A lactone of a compound of formula (I) is represented by formulae (I a) and (I b)

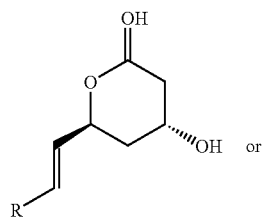
(I a)

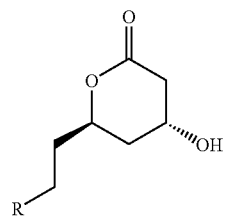
(I b)

Corresponding cyclic residue R comprises a cyclic residue selected from the group consisting of

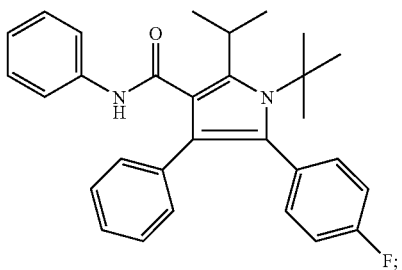

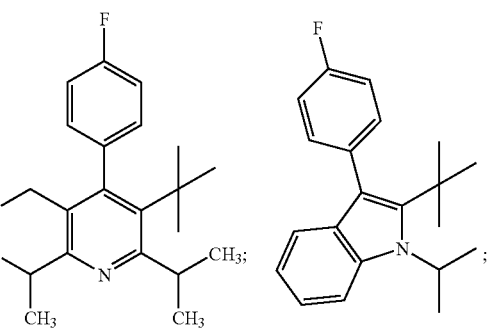

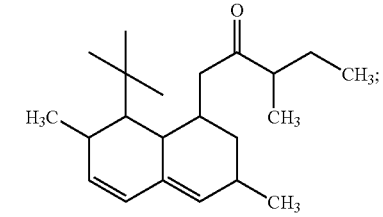

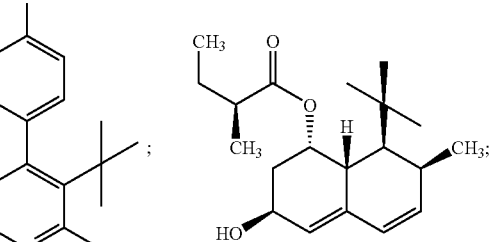

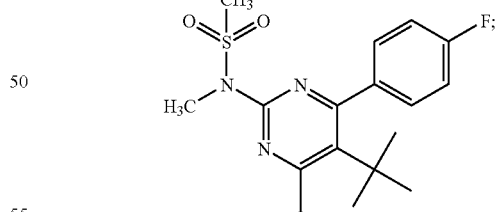

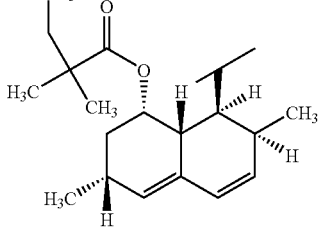

Extensive experimental evaluations surprisingly resulted in a process sequence for the manufacture that meets the above criteria showing the indicated advantages.

The process as disclosed in Bioorganic & Medicinal Chemistry Letters 9 (1999) 2977–2982 for the manufacture of pitavastatin (NK 104) requires the formation of a racemic erythro-β,δ-dihydroxyester that is hydrolysed to form the corresponding acid. With α-methylbenzylamine a diastereomeric mixture of resulting salts are formed that need to be resolved into the different diastereomeric salts. The clear disadvantage of this approach is that half of the material needs to be distroyed. Accordingly, the process of the present invention can be carried out without such a diastereomeric resolution procedure.

The process for the manufacture of a compound of formula

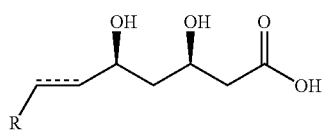

(I)

or a salt thereof or a lactone thereof, wherein the element

- - - - - represents —CH$_2$—CH$_2$— or —CH═CH— and R represents a cyclic residue, according to the present inventions is characterized by (a) reacting a compound of formula (II a)

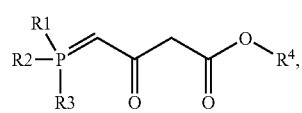

(II a)

wherein $R^1$, $R^2$ and $R^3$, independently of one another, represents phenyl that is un-substituted or substituted by one or more substituents selected from the group consisting of $C_1$–$C_7$alkyl, hydroxy, $C_1$–$C_7$alkoxy, $C_2$–$C_8$alkanoyl-oxy, halogen, nitro, cyano, and $CF_3$, and $R^4$ is an aliphatic, cycloaliphatic, araliphatic or aromatic residue;

with a compound of formula R—CH(═O) (II b) wherein R represents a cyclic residue; and (b) reducing a resulting compound of formula (II c)

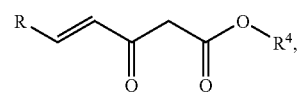

(II c)

wherein R and $R^4$ have the meanings as defined above; in the presence of a reducing agent selected from the group consisting of a compound of formulae (II d), (II d'), (II d''), (II d'''), (II d''''), (II d'''''), and (II d'''''')

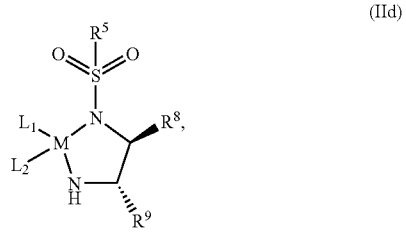

(IId)

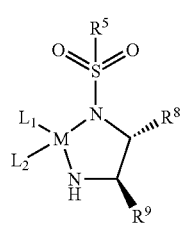

(IId')

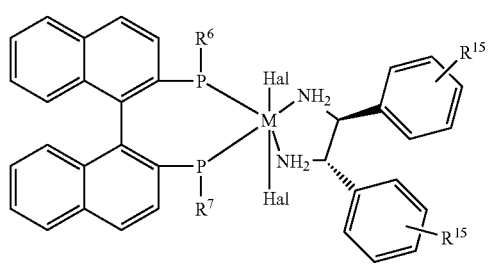

(IId'')

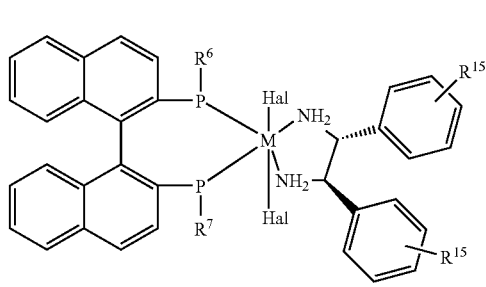

(IId''')

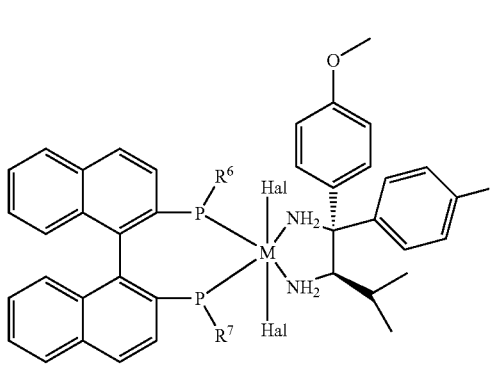

(IId'''')

-continued

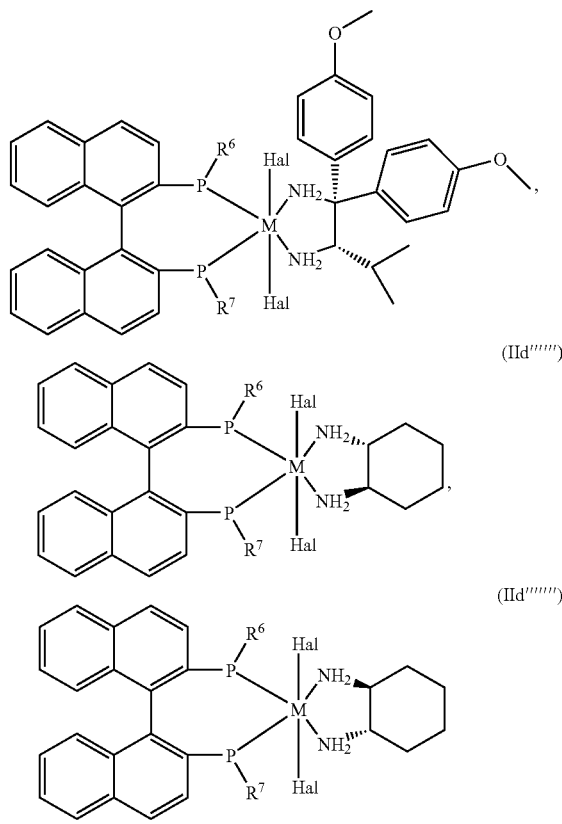

wherein
M is Ru, Rh, Ir, Fe, Co or Ni;
L₁ is hydrogen;
L₂ represents an aryl or aryl-aliphatic residue;
Hal is halogen;
$R^5$ is an aliphatic, cycloaliphatic, cycloaliphatic-aliphatic, aryl or aryl-aliphatic residue, which, in each case, may be linked to a polymer;
each of $R^6$ and $R^7$, independently, is an aliphatic, cycloaliphatic, cycloaliphatic-aliphatic, aryl or aryl-aliphatic residue;
each of $R^8$ and $R^9$ is phenyl or $R^8$ and $R^9$ form together with the carbon atom to which they are attached a cyclohexane or cyclopentane ring; and
$R^{15}$ is H, halogen, amino, nitro or $C_1$–$C_7$alkoxy;
wherein any aromatic residue of a compound of formula (IId), (IId'), (IId''), (IId'''), (IId''''), (IId'''''), (IId'''''') or (IID''''''') is unsubstituted or substituted;
wherein for compounds of formula (IId''), (IId'''), (IId''''), (IId'''''), (IId'''''') or (IID''''''') also combinations with (R)- or (S)-BINAP are possible; and
(c) condensing a resulting compound of formula (II e)

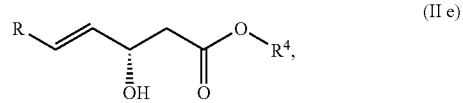

wherein R and $R^4$ have the meanings as defined above, with a compound of formula (II f)

wherein $R^{16}$ represents an aliphatic residue, and
(d) reducing a resulting compound of formula (II g)

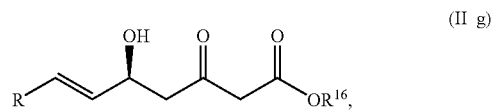

wherein R and $R^{16}$ have the meanings as defined above, and
(e) hydrolysing a resulting compound of formula (II h)

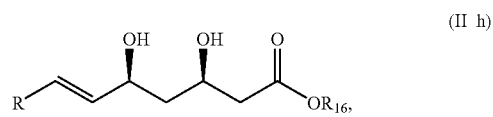

wherein R and $R^{16}$ have the meanings as defined above, and
(f) isolating a resulting compound of formula (I) or a salt thereof; and, if desired, converting a resulting free acid of formula (I) into a salt thereof or into a lactone of formula (I a) or (I b), respectively, or converting a resulting lactone of a formula (I a) or (I b) into an acid of formula (I) or a salt thereof, or converting a resulting compound of formula (I) wherein the element

----- represents —CH═CH— into a compound of formula (I) wherein the element

----- represents —CH₂—CH₂—.
The general terms used hereinbefore and hereinafter have the following meanings, unless defined otherwise.
$C_1$–$C_7$Alkyl is for example methyl, ethyl, n-propyl, isopropyl, n-butyl, isobutyl, sec-butyl, tert-butyl or a corresponding pentyl, hexyl or heptyl residue. $C_1$–$C_4$alkyl, especially methyl or tert-butyl is preferred.
$C_1$–$C_7$Alkoxy is for example methoxy, ethoxy, n-propyloxy, isopropyloxy, n-butyloxy, isobutyl-oxy, sec-butyloxy, tert-butyloxy or a corresponding pentyloxy, hexyloxy, or heptyloxy residue. $C_1$–$C_4$alkoxy is preferred. Especially preferred is methoxy and tert-butoxy.
$C_2$–$C_8$Alkanoyl in $C_2$–$C_8$alkanoyl-oxy is in particular acetyl, propionyl, butyryl, isobutyryl or pivaloyl. $C_2$–$C_5$Alkanoyl is preferred.

Halogen is in particular halogen with an atomic number up to and including 35, i.e. fluorine, chlorine or bromine, and in a broader sense includes iodine. Fluorine or chlorine is preferred.

An aliphatic hydrocarbon residue is, for example, $C_1$–$C_7$alkyl, $C_2$–$C_7$alkenyl or secondarily $C_2$–$C_7$alkynyl.

$C_2$–$C_7$Alkenyl is in particular $C_3$–$C_7$alkenyl and is, for example, 2-propenyl or 1-, 2- or 3-butenyl. $C_3$–$C_5$alkenyl is preferred.

$C_2$–$C_7$-Alkynyl is in particular $C_3$–$C_7$alkynyl and is preferably propargyl.

A cycloaliphatic residue is, for example, a $C_3$–$C_8$cycloalkyl or, secondarily, $C_3$–$C_8$cycloalkenyl. $C_3$–$C_8$Cycloalkyl is, for example, cyclopropyl, cyclobutyl, cyclopentyl, cyclohexyl and cycloheptyl. Cyclopentyl and cyclohexyl are preferred.

$C_3$–$C_8$Cycloalkenyl is in particular $C_3$–$C_7$cycloalkenyl and is preferably cyclopent-2-en-yl and cyclopent-3-enyl, or cyclohex-2-en-yl and cyclohex-3-en-yl.

A cycloaliphatic-aliphatic residue is, for example, $C_3$–$C_8$cycloalkyl-$C_1$–$C_7$alkyl, preferably $C_3$–$C_6$-cycloalkyl-$C_1$–$C_4$alkyl. Preferred is cyclopropylmethyl.

An araliphatic residue is in particular phenyl-$C_1$–$C_7$alkyl, also phenyl-$C_2$–$C_7$alkenyl or phenyl-$C_2$–$C_7$alkynyl.

An aromatic residue is, for example, a carbocyclic or heterocyclic aromatic residue, in particular phenyl or in particular an appropriate 5- or 6-membered and monocyclic residue which has up to four identical or different hetero atoms, such as nitrogen, oxygen or sulfur atoms, preferably one, two, three or four nitrogen atoms, an oxygen atom or a sulfur atom. Appropriate 5-membered heteroaryl residues are, for example, monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered residues are in particular pyridyl.

Pyrrolyl is, for example, 2- or 3-pyrrolyl. Pyrazolyl is 3- or 4-pyrazolyl. Imidazolyl is 2- or 4-imidazolyl. Triazolyl is, for example, 1,3,5-1H-triazol-2-yl or 1,3,4-triazol-2-yl. Tetrazolyl is, for example, 1,2,3,4-tetrazol-5-yl, furyl is 2- or 3-furyl and thienyl is 2- or 3-thienyl, while suitable pyridyl is 2-, 3- or 4-pyridyl.

Appropriate multicyclic residues are anthracenyl, phenanthryl, benzo[1,3]-dioxole or pyrenyl. An aryl residue may be mono-substituted by e.g. $NH_2$, OH, $SO_3H$, CHO, or di-substituted by OH or CHO and $SO_3H$.

Any aromatic residue is preferably unsubstituted or substituted, for example, by one or more, e.g. two or three, residues e.g. those selected from the group consisting of $C_1$–$C_7$alkyl, hydroxy, $C_1$–$C_7$alkoxy, $C_2$–$C_8$alkanoyl-oxy, halogen, nitro, cyano, and $CF_3$.

Polymers may be polystyrene (PS), cross-linked PS (J), polyethylene glycol (PEG) or a silica gel residue (Si). Examples are NH—$R^{15}$ wherein $R^{15}$ is $C(O)(CH_2)_n$—PS or $C(O)NH(CH_2)_n$—PS; and —O—$Si(R^{14})_2(CH_2)_nR^{16}$ wherein n is 1 to 7, $R^{14}$ is $C_1$–$C_6$alkyl, e.g. ethyl, and $R^{16}$ is a PS, J, PEG or Si (obtainable by Aldrich, Switzerland).

In formula formula (IId), (IId'), (IId''), (IId'''), (IId''''), (IId'''''), (IId'''''') or (IID''''''') the following significances are preferred independently, collectively or in any combination or sub-combination:

M is Ru, Rh, Ir, preferably Ru.

$L_2$ is isopropylmethylbenzene, benzene, hexamethylbenzene, mesitylene, preferred is isopropylmethylbenzene.

$R^5$ is 2- or 3- or 4-pyridyl, 4-chloro-4-phenoxy-phenyl, 4-phenoxy-phenyl, 5-di(m)ethylamino-1-naphthyl, 5-nitro-1-naphthyl, 2-, 3-, 4-nitrophenyl, 4-vinylphenyl, 4-biphenylyl, 9-anthra 2,3 or 4 hydroxyphenyl, tolyl, phenanthryl, benzo[1,3]-dioxole, dimethyl(naphthalene-1-yl)-amine, mono to tristrifluoromethylphenyl, chrysenyl, perylenyl or pyrenyl or 2-phenylethene.

Each of $R^6$ and $R^7$, independently, are phenyl, 4-methylphenyl or 3,5-dimethylphenyl, preferred is phenyl.

Each of $R^8$ and $R^9$ is phenyl or cyclohexyl or substituted phenyl, preferably is phenyl.

Preferred Hal is chloro.

Preferred $R^{15}$ is H.

$L_1$ is as defined above.

In a preferred aspect, the invention provides a process for the production of a compound of formula I'a or I'b The reactions described above and below in the variants are carried out, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

Preferably, in the process according to the present invention compounds of formulae (II a), (II c), (II e), (II f), (II g) and (II h) are used, wherein $R^4$ or $R^{16}$, respectively, represent $C_1$–$C_4$alkyl, especially methyl or ethyl or most preferably tert-butyl.

Step (a):

In reaction Step (a), the reaction of a compound of formula (II a) with a compound of formula (II b) is carried out in a suitable inert solvent, such as a nitrile, especially acetonitrile or propionitrile, and in a temperature range from, for example, from −78° C., to the boiling point of the solvent, preferably at the boiling point of the solvent.

Step (b):

Reaction Step (b) is an asymmetric transfer hydrogenation, especially when using a chiral Ru(II) catalyst of formula (II d) and a hydrogen donor.

Step (b) is carried out in a suitable inert solvent, such as an ether, e.g. tetrahydrofuran, an ester, such as ethylacetate, an nitrile, especially acetonitrile, a formamide, especially dimethylformamide, and in a temperature range from, for example, from −78° C., to the boiling point of the solvent, preferably at room temperature.

Preferred catalysts are following compounds

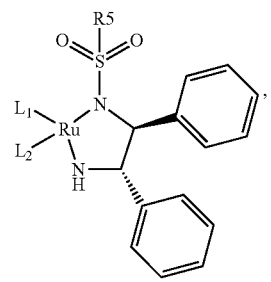

-continued

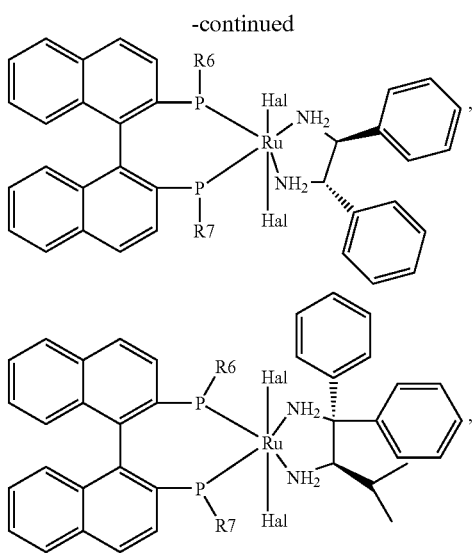

wherein $L_1$ is hydrogen and $L_2$ represents an aliphatic, cycloaliphatic, cycloaliphatic-aliphatic, aryl or araliphatic residue; Hal is halogen; $R^5$, $R^6$ and $R^7$, independently of one another, represents an aliphatic, cycloaliphatic, cycloaliphatic-aliphatic, aryl or araliphatic residue; wherein, in each case, any aromatic residue of a compound of formulae (II d), (II d') and (II d") is unsubstituted or substituted;

Preferred Ru (II) catalysts of formula (II d) are those wherein $L_1$ is hydrogen and $L_2$ is isopropylphenyl, $R^5$ is tolyl.

A preferred hydrogen donor is, for example, $NEt_3/H_3PO_2/H_2O$, diphenylsilan/MeOH or a system comprising 2-propanol, 3-pentanol, or most preferably HOOCH in the presence of an amine, such as triethylamine, DBU or other tertiary amines. The hydrogen donor may also be used as inert solvent, especially 2-propanol and most preferably HCOOH. An alternative hydrogen donor is 2-propanol in the presence of various catalysts and base, e.g. Ru[(1S,2S)-p-TsNCH($C_6H_5$)CH($C_6H_5$)NH]($\eta^6$-p-cymene) and base or "in situ" [Ru($\eta^6$-p-cymene)$Cl_2$]$_2$ with chiral ligand (R,R- or S,S-TsDPEN, amino-alcohol) and base. The preferred bases are: t-BuOK, KOH or i-PrOK.

A preferred hydrogen donor is, for example, a system comprising HOOCH in the presence of an amine, such as triethylamine, or most preferably 2-propanol. The hydrogen donor may also be used as inert solvent, especially HCOOH and most preferably 2-propanol.

Step (b) can also be carried out by hydrogenating with hydrogen in the presence of a catalyst of formula (II d') or (II d"), (IId"'), (IId""), (IId"""), (IId"""") or (IID""""), respectively. A suitable inert solvent is e.g. an ether, such as tetrahydrofuran, an ester, such as ethylacetate, or an alcohol, such as a $C_1$–$C_4$alkanol, for example, isopropanol.

Preferred Hal is chloro.

Step (c):

Condensation Step (c) is carried out in the presence of a condensation system and in a suitable inert solvent, such as an ether, especially tetrahydrofuran or tert-butyl-ethyl ether, and in a temperature range from, for example, from −78° C., to the boiling point of the solvent, preferably at room temperature.

A suitable condensating system is, for example, a base, such as an alkane alkalimetal, especially butyl lithium, or a hydride, e.g. sodium hydride, or a mixture thereof. Especially preferred is the use of the condensation system butyl lithium in the presence of diisopropylamine.

Step (d):

A preferred reduction agent is, for example, a hydride, for example, an alkalimetal borohydrid, especially sodium borohydride, preferably in the presence of a di-$C_1$–$C_7$alkyl-$C_1$–$C_7$alkoxy-borane, most preferably diethyl-methoxy-borane.

The reduction is carried out in an inert solvent, such as an ether, preferably tetrahydrofuran, and at low temperatures, for example, from −780° to 0° C., preferably at −78° C. To split a corresponding boronic ester the reaction mixture is then oxidized with an oxidizing agent, such as a peroxide, especially, hydrogen peroxide. The oxidation is carried out in an inert solvent, such as an ether, preferably tetrahydrofuran, and in a temperature range from, for example, from 0° C., to the boiling point of the solvent, preferably in a range of 0° to 20° C.

Step (e):

The saponification Step (e) is carried out, for example, by treating the ester of formula (II h) with a strong base, such as an alkali metal hydroxide, preferably NaOH, or with $Ca(OH)_2$ and acidifying the resulting reaction mixture.

Step (f):

The isolation Step (f) of a compound of formula (I) is carried out according to conventional isolation methods, such as by crystallizing the resulting compound of formula (I) from the reaction mixture or by chromatography of the reaction mixture.

Inert solvents are those that do not react with the corresponding reactants.

The present invention likewise relates to a novel compound of formula (II c). Especially preferred are compounds of formula (II c), wherein R is a group of formula

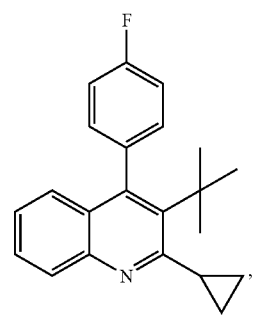

the element

----- represents —CH═CH—, and $R_4$ is $C_1$–$C_4$alkoxy, especially methoxy or ethoxy or tert-butoxy.

The present invention likewise relates to a novel compound of formula (II c). Especially preferred are compounds of formula (II c), wherein R is a group of formula the element

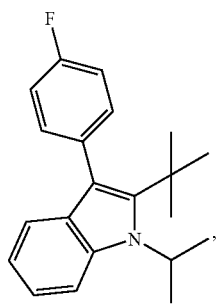

represents —CH=CH—, and $R^4$ is $C_1$–$C_4$alkoxy, especially methoxy or ethoxy or tert-butoxy.

It is known from the art that asymmetric transfer hydrogenation using a Ru (II) catalyst (esp. a Noyori catalyst) is carried out in the absence of water and under inert gas conditions. Surprisingly, the transfer hydrogenation step according to the present invention can be run in a water containing solvent system and in the absence of an inert gas. This means that the reaction is successful even though the solvent used comprised water (e.g. 3% by Karl-Fischer).

Furthermore, the compound of formula (II c) could—in view of the esterified carboxy group—be a ligand of the Ru (II) catalyst as well. Surprisingly, it has been proven that a compound of formula (II c) does not form a ligand to the Ru catalyst.

It is known that quinoline moieties are desactivating the hydrogenation catalysts. Especially, in case of the manufacture of compound of (I) being pitavastatin, the person skilled in the art would expect that the quinoline group desactivates the Ru catalyst. Surprisingly, the asymmetric transfer hydrogenation step according to the present invention is successfully carried out without that the catalyst of formulae (II d), (II d'), (II d"), (IId'''), (IId""), (IId""'), (IId"""') or (IId""""') is being desactivated.

Accordingly, the present invention also relates to reaction step (b), especially when using a Ru(II) catalyst of formulae (II d), (II d') or (II d"), respectively.

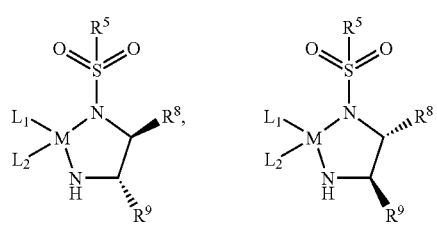

wherein M, $L_1$, $L_2$, $R^8$ and $R^9$ are as defined above and $R^5$ is a group of formula

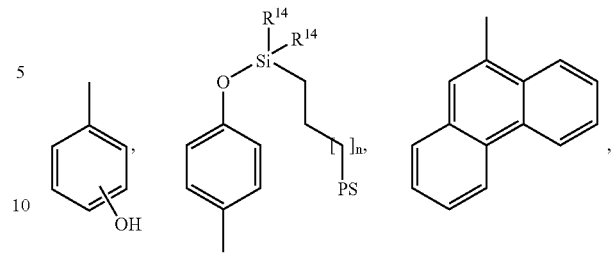

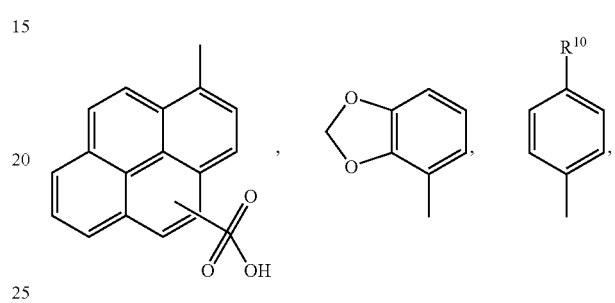

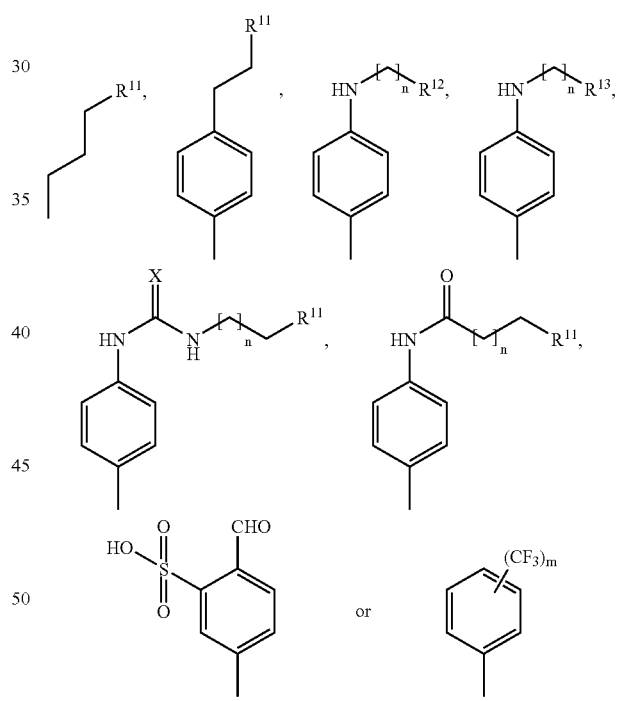

wherein
n is 0, 1, 2, 3, 4, 5, 6 or 7;
X is O or S;
$R^{10}$ is polystyrol;
$R^{11}$ is silica gel;
$R^{12}$ is cross-linked polystyrol;
$R^{13}$ is polyethylene-glycol;
$R^{14}$ is $C_1$–$C_6$alkyl; and
m is 1, 2 or 3.

The following compounds of formula (IId), (IId'), (IId''') or (IId'''') wherein $L_1$, $L_2$ and $R^5$ are as defined above, are preferred:

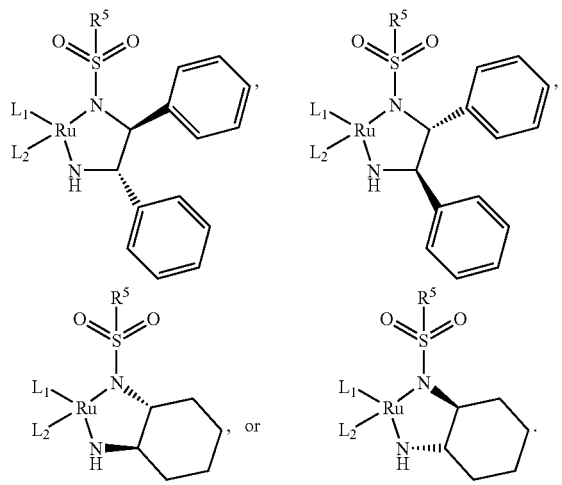

Compounds of formula (IId), (IId'), (IId''') or (IId'''') may be prepared by reacting a compound of formula VII

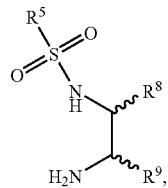

(VII)

wherein $R^5$, $R^8$ and $R^9$ are as defined above, with $[MCl_2(p\text{-cymene})]_2$ in conventional manner. The hydrogenation may be carried out in a suitable inert solvent, such as an ether, e.g. tetrahydrofuran, an ester, such as ethylacetate, a halogenated solvent, such as methylenchloride, supercritical $CO_2$, ionic liquids, a nitrile, especially acetonitrile, an amide, such as dimethylformamide or dimethylacetamide and in a temperature range from, for example, from −78° C., to the boiling point of the solvent, preferably at room temperature.

Preferred catalysts of formula (II d) are those, wherein $L_1$ is hydrogen and $L_2$ represents phenyl or phenyl substituted by one, two, three, four or five alkyl residues, especially by once by isopropyl such as 4-isopropyl-phenyl, and $R^5$ represents phenyl or phenyl substituted by one, two, three, four or five alkyl residues, especially phenyl, tolyl, 3,5-dimethylphenyl, or 2,3,4,5,6-pentamethyl-phenyl. Especially preferred is the catalyst of formula (II d) or (Id'), wherein $L_1$ is hydrogen, $L_2$ is isopropylphenyl, and $R^5$ is tolyl.

The present invention likewise relates to preferred catalysts of formula (II d) being those, wherein $L_1$ is hydrogen and $L_2$ represents phenyl or phenyl substituted by one, two, three, four or five alkyl residues, especially by once by isopropyl such as isopropyl-phenyl, and $R_5$ represents a residue selected from the group consisting of 2- or 3- or 4-pyridyl, 4-chloro-4-phenoxy-phenyl, 4-phenoxy-phenyl, 5-di(m)ethylamino-1-naphthyl, 5-nitro-1-naphthyl, 2-, 3-, 4-nitrophenyl, 4-vinylphenyl, 4-biphenylyl, 2-phenyl-ethen and 9-anthracenyl.

Especially preferred are those catalysts of formula (IId), wherein the ligands $L_1$ and $L_2$ have the S or R configuration and/or wherein the corresponding phenyl rings attached to the 1,2-diaminoethyl moiety are in the R,R-configuration or S,S-configuration.

Preferred catalysts of formula (II d') and (IId''') are those, wherein Hal is each case is chloro; $R^6$ and $R^7$, in each case, represents phenyl or phenyl substituted by one or more $C_1$–$C_7$alkyl, especially 3,5-dimethylphenyl. The present invention likewise relates to corresponding compounds of formula (II d'). Especially preferred are those catalysts of formula (II d'), wherein the BINAP moiety has the R- or S-configuration.

Preferred catalysts of formula (II d'') and (IId'''') are those, wherein Hal, in each case, is chloro; $R^6$ and $R^7$, in each case, represents phenyl or phenyl substituted by one or more $C_1$–$C_7$alkyl, especially 3,5-dimethylphenyl. The present invention likewise relates to corresponding compounds of formula (II d'''') and (Iid'''''). Especially preferred are those catalysts of formula (II d'''') and (IId'''''), wherein the BINAP moiety has the R- or S-configuration. Most preferred are corresponding compounds of formula (II d'''') and (IId'''').

Likewise preferred are compounds of formula

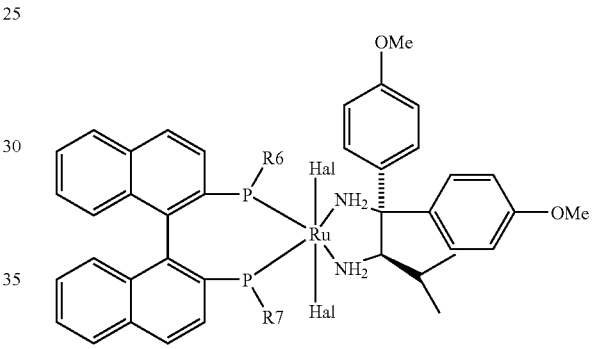

The present invention likewise relates to the novel compounds, e.g. starting materials or intermediates, respectively, as described in the Working Examples part.

The present invention likewise relates to the concrete products directly obtained by the process sequence or by the single process steps, especially the corresponding products that are in an essentially enantiomerically pure form.

The conversion of an acid of formula (I) into a salt is carried out in a manner known per se. Thus, for example, a salt with a base of compounds of the formula I is obtained by treating with a base. Salts can be converted into the free compounds in a customary manner, and salts with a base can be converted, for example, by treating with a suitable acid agent to the free acid.

The conversion of an acid of formula (I) into a corresponding lactone of formula (I a) or (I b), respectively, is carried out in the presence of an acid, preferably a mineral acid, in a suitable, e.g. protic or aproctic, solvent, such as ethanol or acetonitrile. Depending on the acid, the conversion is carried out in a temperature range, for example, from −78° to the boiling point of the solvent. Most preferably, $H_3PO_4$ in acetonitrile at 60° C. is used.

The conversion of a lactone of formula (I a) or (I b), respectively, into a salt of the acid of formula (I) is carried out, for example, in a mixture of a protic solvent, e.g. ethanol, and water, by using an alkalimetall hydroxide, such as LiOH, NaOH or $Ca(OH)_2$. Alternatively, the lactone can be hydrolysed by using an alkalimetall hydroxide, such as LiOH, NaOH and the resulting salt can be converted into the calcium salt of the acid of pitavastatin by addition of an aqueous solution of $CaCl_2$ in water.

A variant to the process according to the present invention comprises the direct formation of a lactone of a compound of formula (I). The formation of said lactone can be carried out by treating a compound of formula (I) or (II h) with an acid, such as a mineral acid, preferable with $H_3PO_4$.

The conversion of a resulting compound of formula (I) wherein the element

----- represents —CH═CH— into a compound of formula (I) wherein the element

----- represents —CH$_2$—CH$_2$— is carried out by selectively hydrogenating the double bond —CH═CH—, especially with an appropriate reduction agent, for example, by catalytic hydrogenation in the presence of a hydrogenation catalyst, for example, a Ruthenium catalyst, such as (Ru(cod)(nu-3-(2-methylally))2, by reduction with hydrogen in the presence of a hydrogenation catalyst or with a hydride, for example, a hydride which, if desired, may be complex, such as a hydride formed from an element of the 1st and 3rd main groups of the periodic table of the elements, for example borohydride or aluminohydride, for example lithium borohydride, lithium aluminium hydride, diisobutylaluminium hydride (an additional reduction step using alkali metal cyanoborohydride, such as sodium cyanoborohydride, may be necessary), and also diborane.

Instead of converting a resulting compound of formula (I) wherein the element

----- represents —CH═CH— into a compound of formula (I) wherein the element

----- represents —CH$_2$—CH$_2$—, the hydrogenation of the double bond —CH═CH— can be effected, with compounds of formulae (II e), (II g) or (II h), respectively, e.g. in addition to reaction steps (c), (d) or (e), respectively.

The process for the manufacture of compounds of formula (I) and salts thereof can be, for example, illustrated by means of the following reaction scheme for the manufacture of pitavastatin:

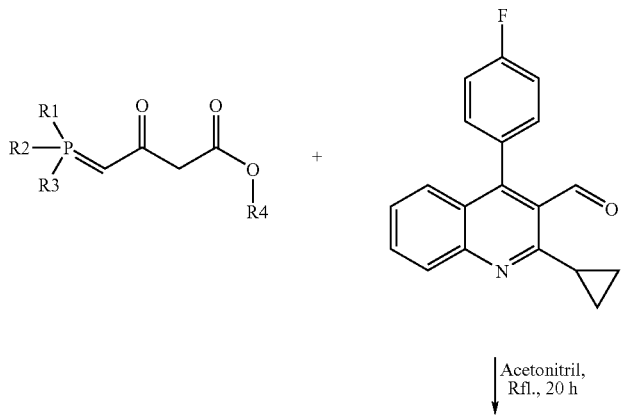

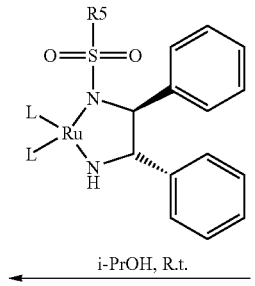
-continued
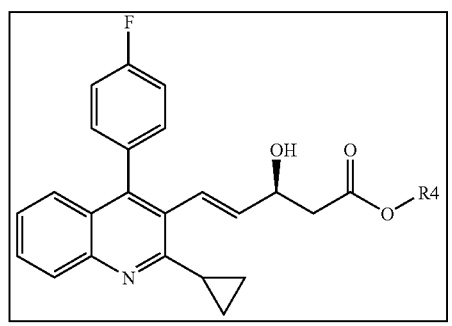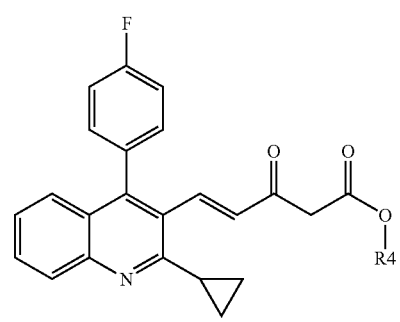
i-PrOH, R.t.
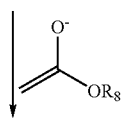
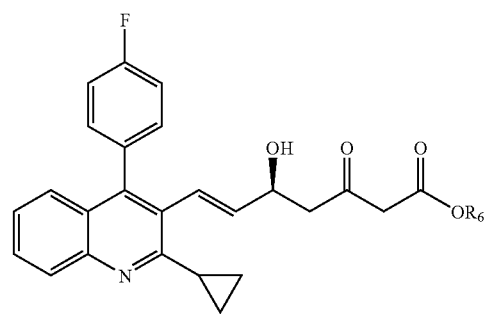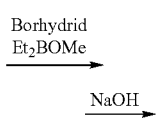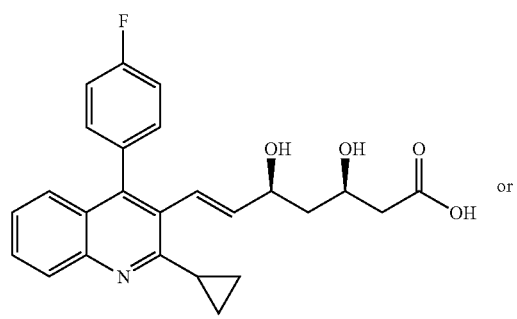
Borhydrid Et₂BOMe / NaOH
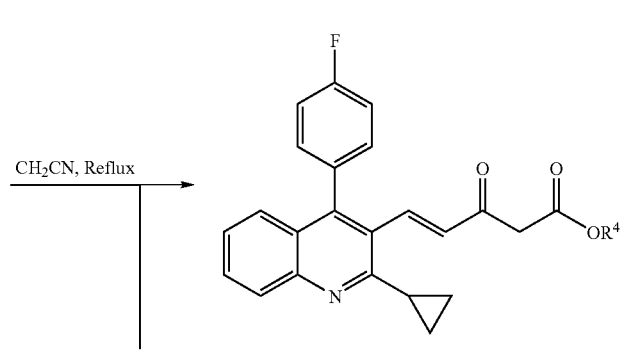
CH₃CN, Reflux
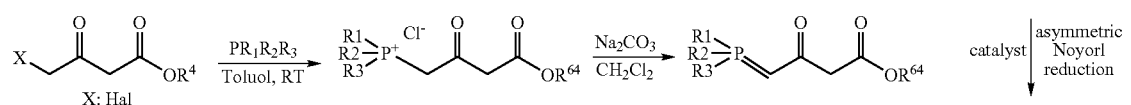

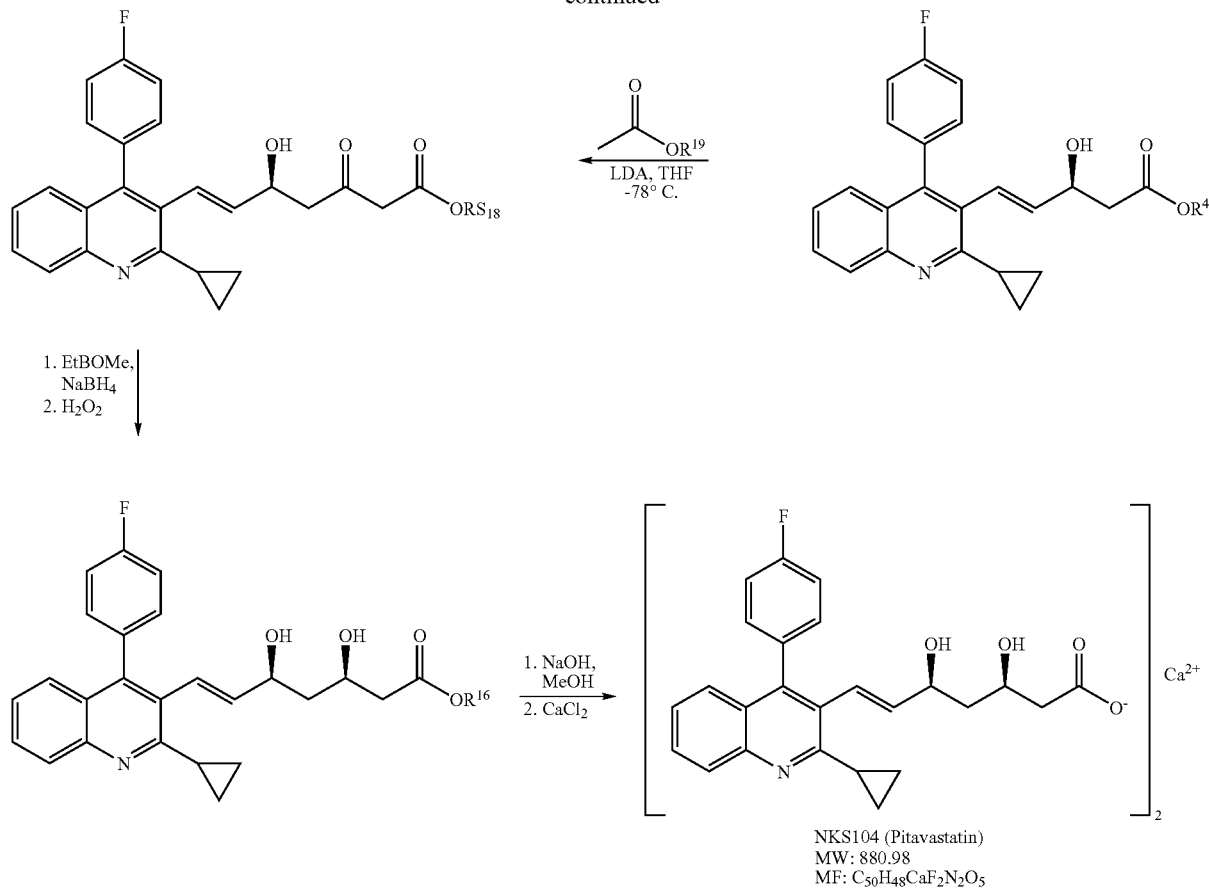
The process for the manufacture of compounds of formula (I) and salts thereof can be, for example, illustrated by means of the following reaction scheme for the manufacture of fluvastatin:
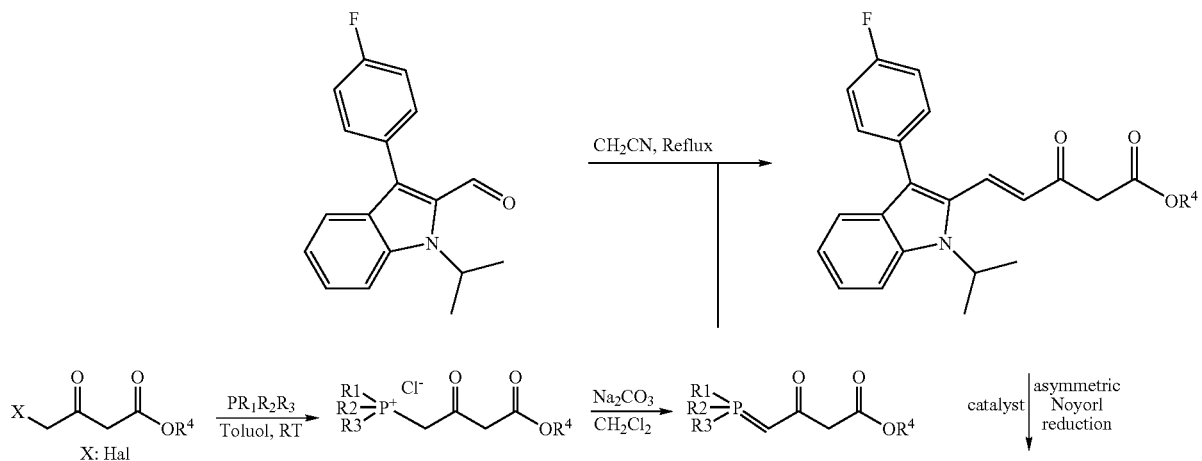

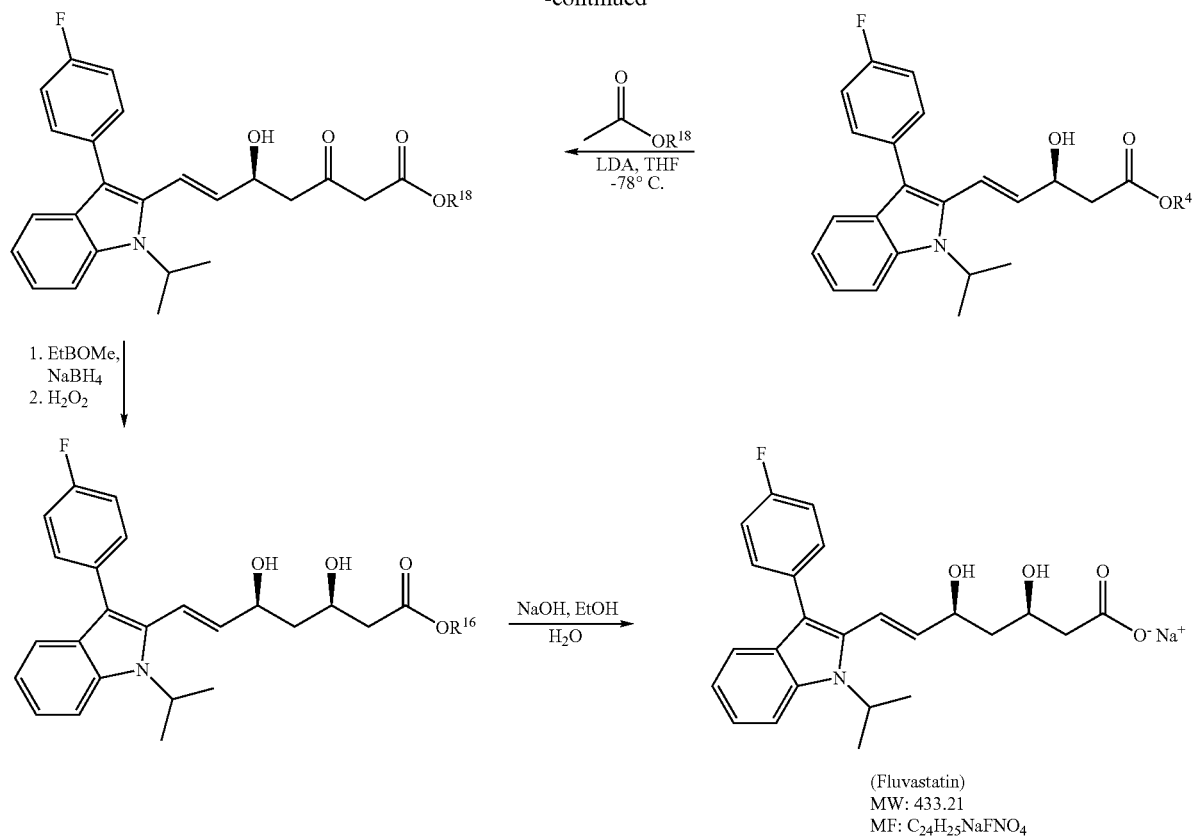

(Fluvastatin)
MW: 433.21
MF: $C_{24}H_{25}NaFNO_4$

WORKING EXAMPLES

Manufacture of Starting Material for Pitavastatin:

Preparation of (3-ethoxycarbonyl-3-oxopropyl)triphenyl phosphonium chloride

According to Literature: C. M. Moorhoff; J. C. S. Perkin Trans I, 1987 (1997)

To a solution of ethyl-4-chlor-acetoacetat (16.46 g, 100 mmol) in 50 ml anhydrous toluene is added triphenylphosphine (26.25 g, 100 mmol) under argon atmosphere at room temperature and stirred for 4 days. The suspension is filtered and washed with 3×30 ml of toluene. The colourless crystals are dried in vacuum to give (3-ethoxycarbonyl-3-oxopropyl) triphenyl phosphonium chloride. MS: 426.88

Example 1 a) Preparation of ethyl 3-oxo-4-(triphenylphosphoranylidene)butanoate

To a solution of (3-ethoxycarbonyl-3-oxopropyl)triphenyl phosphonium chloride (11 g, 25.77 mmol) in 100 ml dichlormethane is added within 30 minutes (min) under vigorous stirring sodium carbonate (3.38 g, 27.36 mmol) in 100 ml water at room temperature and stirred for 4 hours (h). The yellow organic phase is separated, washed with 30 ml water and dried over anhydrous sodium sulfate. The solvent is evaporated and the oily residue is dried in vacuum to maintain a waxy mass. After adding diethylether the wax crystallizes to form slight yellow crystals of 3-oxo-4-(triphenylphosphoranylidene)butanoate. MS: 390.43

$^1$H-NMR (CDCl$_3$, 400 MHz): δ=7.56 (m,6H,ortho H-phenyl), 7.44 (m, 3H,para H-phenyl), 7.35 (m, 6H,meta H-phenyl), 4.08 (q, 2H, OCH$_2$CH$_3$), 3.72 (d, 1H, H-4), 3.26 (d, 2H, H-2), 1.17 (t, 3H, OCH$_2$CH$_3$)

b) 5-(2-Cyclopropyl-4-fluoro-phenyl)-quinolin-3-yl)-3-oxo-pent-4-enoic acid ethyl ester The ylide 3-oxo-4-(triphenylphosphoranylidene)butanoate (4.82 g, 12.36 mmol) is solved under argon atmosphere in 100 ml acetonitrile. Under vigorous stirring 2-cyclopropyl-4-(4-fluoro-phenyl)-quinoline-3-carbaldehyde (3 g, 10.3 mmol) is added in 5 portions and then heated to reflux. After 50 h the reaction is cooled to room temperature. The slight brown solvent is evaporated and the residue is dried under vacuum to obtain a brown waxy oil. Chromatography over silica gel with hexane:ethylacetate (4:1/v:v) give a yellow oil of 5-(2-cyclopropyl-4-fluoro-phenyl)-quinolin-3-yl)-3-oxo-pent-4-enoic acid ethyl ester. MS: 403.45 c) rac 5-[2-Cyclopropyl-4-(4-fluoro-phenyl)-quinolin-3-yl]-3-hydroxy-pent-4-enoic acid ethyl ester 85.8 mg (0.21 mmol) of 5-(2-cyclopropyl-4-fluoro-phenyl)-quinolin-3-yl)-3-oxo-pent-4-enoic acid ethyl ester are solved in 10 ml ethanol under argon atmosphere and cooled to −15° C.

Sodiumborhydride (8.58 mg, 0.22 mmol) is added under vigorous stirring. During the reaction time the mixture became slightly yellow. After 3 h the reaction is allowed to rise to room temperature and stirred for another 1.5 h. Then the mixture is quenched with 15 ml of a saturated ammonium chloride solution. After extraction with diethylether (3×15 ml), the combined organic layers are washed with water (15 ml), dried over sodium sulfate, filtered and evaporated in vacuum to give a yellow oil of rac 5-[2-cyclopropyl-4-(4-fluoro-phenyl)-quinolin-3-yl]-3-hydroxy-pent-4-enoic acid ethyl ester. MS: 405.47

HPLC-Analytics: Chiracel-OD 10 μm, length: 250 mm, internal-dm: 4.6 mm; isokratic n-hexane: 2-propanol 96:4; flowrate:0.6 ml/min; column temp:35° C.; UV detection wavelength: 230 nm; chrom.time: 45 min; inject.volume: 10 μl (1.022 mg/ml in n-hexane:2-propanol 96:4)

Ret. Time 1: 16.17 min; 51.52% (area)
Ret. Time 2: 18.00 min; 48.48% (area)

d) Procedure for the enantioselective transfer hydrogenation of (E)-5-[2-Cyclopropyl-4-(4-fluoro-phenyl-quinolin-3-yl]-3-hydroxy-pent-4-enoic-acid-ethylester I: A mixture of (E)-5-[2-cyclopropyl-4-(4-fluoro-phenyl)-quinolin-3-yl]-3-oxo-pent-4-enoic-acid-ethylester (105.8 mg, 0.262 mmol) and Ru[(1R,2R)-p-TsNCH($C_6H_5$)CH($C_6H_5$)NH]($\eta^6$-p-cymene) (6.2 mg, 0.104 mmol) in 2-propanol (2.6 ml) is stirred at 23° C. for 72 h. The reaction mixture is concentrated under reduced pressure. The residue is purified by flash chromatography on silica gel using a 4:1 hexane-MTBE (methyl-tert-butyl-ether) mixture as eluent to afford of (E)-5-[2-Cyclopropyl-4-(4-fluoro-phenyl)-quinolin-3-yl]-3-hydroxy-pent-4-enoic-acid-ethylester.

II: A solution of (E)-5-[2-cyclopropyl-4-(4-fluoro-phenyl)-quinolin-3-yl]-3-oxo-pent-4-enoic-acid-ethylester (1.6 g, 3.97 mmol), Ru[(1R,2R)-p-TsNCH($C_6H_5$)CH($C_6H_5$)NH$_2$]Cl($\eta^6$-p-cymene) (12.6 mg, 0.02 mmol) and a mixture of HCOOH (1.095 g, 23.8 mmol)/NEt$_3$ (0.963 g, 9.52 mmol) is heated in DMF (6.0 ml) at 50° C. for 20 h. After that the solution is diluted with MTBE (5 ml) and neutralised with NaHCO$_3$ (4 ml). Standard aquous work-up with NaCl solution and extraction with MTBE and removal of the solvent give the crude product. Chromatography on silica gel using a 4:1 hexane-MTBE mixture as eluent to afford of (E)-5-[2-Cyclopropyl-4-(4-fluoro-phenyl)-quinolin-3-yl]-3-hydroxy-pent-4-enoic-acid-ethylester.

$^1$H NMR (400 MHz, CDCl$_3$): 7.96 (d, $^2$J: 8.4 Hz, 1H), 7.60 (t, $^2$J: 6.6 Hz, 1H), 7.38–7.28 (m, 2H), 7.25–7.15 (m, 4H), 6.61 (d, $^2$J: 16.3 Hz, 1H), 5.65 (dd, $^2$J: 16.2, 5.7 Hz, 1H), 4.57–4.51 (m, 1H), 4.17 (q, $^2$J: 7.1 Hz, 2H), 3.10 (br s, 1H), 2.44–2.37 (m, 1H), 2.36 (t, $^2$J: 9.4 Hz, 2H), 1.41–1.25 (m, 2H), 1.29 (t, $^2$J: 7.2 Hz, 3H), 1.04 (dd, $^2$J: 8.1, 2.8 Hz, 2H). $^{13}$C NMR (100 MHz, CDCl$_3$): 172.2, 163.6, 161.1, 160.7, 146.9, 144.4, 138.2, 133.4, 132.0, 131.9, 131.9, 131.8, 129.0, 128.9, 126.5, 126.1, 125.5, 115.5, 115.3, 68.8, 41.1, 16.1, 14.2, 10.4, 10.3. MS: 405.47

Literature for the preparation of the catalyst: Haack, K.-J.; Hashiguchi, S.; Fujii, A.; Ikariya, T.; Noyori, R. *Angew. Chem., Int. Ed. Engl.* 1997, 36, 285–288.

e) (E)-(S,-7-[2-Cycloproryl-4-(4-fluoro-phenyl)-quinolin-3-yl]-5-hydroxy-3-oxo-hept-6-enoic acid tert-butyl ester To a solution of diisopropylamine (0.93 g, 9.20 mmol) in tetrahydrofuran (THF) (10 ml) at 0° C. is added nBuLi (5.55 ml, 8.88 mmol of a 1.6 M solution in hexane) over 10 min. After 30 min the solution is cooled to −78° C. and t-butyl acetate (1.03 g, 8.88 mmol) is added over 10 min. After 30 min the resulting solution at −78° C. is transferred to a solution of (E)-5-[2-cyclopropyl-4-(4-fluoro-phenyl)-quinolin-3-yl]-3-hydroxy-pent-4-enoic-acid-ethylester (0.90 g, 2.22 mmol) in THF (11 ml) at 0° C. The solution is stirred 3 h at room temperature (RT). A NH$_4$Cl solution (3 ml) is added. The mixture is poured into water (5 ml) and extracted with MTBE (50 ml). The combined organic extracts are dried over Na$_2$SO$_4$, filtered, concentrated, and the residue purified by flash chromatography (hexane/MTBE 5:1) to afford ketoester (E)-(S)-7-[2-cyclopropyl-4-(4-fluoro-phenyl)-quinolin-3-yl]-5-hydroxy-3-oxo-hept-6-enoic acid tert-butyl ester. MS: 475.57 f) (E)-(3R,5S)-7-[2-Cylopropyl-4-(4-fluoro-phenyl)-quinolin-3-yl]-3,5-dihydroxy-hept-6-enoic acid tert-butyl ester To a solution of ketoester (E)-(S)-7-[2-cyclopropyl-4-(4-fluoro-phenyl)-quinolin-3-yl]-5-hydroxy-3-oxo-hept-6-enoic acid tert-butyl ester (0.80 g, 1.68 mmol) in THF (20 ml) and MeOH (4 ml) at −78° C. is added diethylmethoxyborane (2.10 ml of a 1 M solution in THF, 2.096 mmol). After 1 h NaBH$_4$ (0.127 g, 3.36 mmol) is added. After an additional 3 h at −78° C. pH 7 buffer (5 ml) is added followed by MeOH (6 ml). After 10 min a solution of MeOH (6 ml) and 30% aqu. H$_2$O$_2$ (6 ml) is added slowley. The cold bath is removed and the solution stirred for 1.5 h. The mixture is poured into NaHCO$_3$ (60 ml) and extracted with CH$_2$Cl$_2$ (3×50 ml). The organic extracts are dried over Na$_2$SO$_4$, filtered, and concentrated. The residue is dissolved in hot EtOAc (10 ml), filtered and stirred for 12 h at RT. After filtration diol (E)-(3R,5S)-7-[2-cyclopropyl-4-(4-fluoro-phenyl)-quinolin-3-yl]-3,5-dihydroxy-hept-6-enoic acid tert-butyl ester is obtained. MS: 477.58 g) (E)-(3S,5S)-7-[2-Cyclopropyl-4-(4-fluoro-phenyl)-quinolin-3-yl]-3,5-dihydroxy-hept-6-enoic acid tert-butyl ester To a cooled (−35° C.) solution of Me$_4$NHB(OAc)$_3$ (1.38 g, 5.26 mmol) in MeCN/AcOH (15 ml, 1:1) is added a solution of ketoester (E)-(S)-7-[2-cyclopropyl-4-(4-fluoro-phenyl)-quinolin-3-yl]-5-hydroxy-3-oxo-hept-6-enoic acid tert-butyl ester (0.50 g, 1.05 mmol) in CH$_3$CN (2 ml). The mixture is stirred at −35° C. for 3 h and at 0° C. for 30 min before a solution of potassium sodium tartrate (10 ml) is added. After 10 min the suspension is poured into CH$_2$Cl$_2$ (30 ml) and a solution of Na$_2$CO$_3$ (7 ml) is carefully added. The organic layer is separated and the aqueous layer is extracted with CH$_2$Cl$_2$ (2×50 ml). The combined organic extracts are dried over Na$_2$SO$_4$, filtered, concentrated, and the residue is purified by flash chromatography (hexane/MTBE 1:1) or crystallization (ethylacetate=EtOAc) to afford diol (E)-(3R,5S)-7-[2-cyclopropyl-4-(4-fluoro-phenyl)-quinolin-3-yl]-3,5-dihydroxy-hept-6-enoic acid tert-butyl ester. MS: 477.58 h) (E)-(3R,5S)-7-[2-Cyclopropyl-4-(4-fluoro-phenyl)-quinolin-3-yl]-3,5-dihydroxy-hept-6-enoic acid calcium salt To a solution of diol (E)-(3R,5S)-7-[2-cyclopropyl-4-(4-fluoro-phenyl)-quinolin-3-yl]-3,5-dihydroxy-hept-6-enoic acid tert-butyl ester (1.0 g, 2.09 mmol) in EtOH (5 ml) is added an aquous solution of NaOH (10 ml, 1 M) and the resulting suspension is stirred until the ester disappeared. After completion of the hydrolysis aqueous HCl (15 ml, 1 M) is added and the solvent is removed in vaccum. Then $CH_2Cl_2$ (10 ml) is added and the organic layer is separated. The aqueous layer is extracted with $CH_2Cl_2$ (2×30 ml) and the combined organic extracts are removed in vaccum. The residue is dissolved in $H_2O$ (20 ml) and a solution of $CaCl_2$ (8 ml, 0.1 M) is added dropwise. The reaction solution is stirred overnight and the resulting white precipitate is collected by filtration to obtain (E)-(3R,5S)-7-[2-cyclopropyl-4-(4-fluoro-phenyl)quinolin-3-yl]-3,5-dihydroxy-hept-6-enoic acid calcium salt. MS: 880.98

Manufacture of Starting Material for Fluvastatin:

i. (E)-5-[3-(4-Fluoro-phenyl)-1-isopropyl-1H-indol-2-yl]-3-oxo-pent-4-enoic acid ethyl ester The ylide 3-oxo-4-(triphenylphosphoranylidene)butanoate (5.0 g, 12.8 mmol) is solved under argon atmosphere in 100 ml acetonitrile. Under vigorous stirring 3-(4-Fluoro-phenyl)-1-isopropyl-1H-indole-2-carbaldehyde (4.2 g, 10.7 mmol) is added in 5 portions and then heated to reflux. After 50 h the reaction is cooled to room temperature. The slight brown solvent is evaporated and the residue is dried under vacuum to obtain a brown waxy oil. Chromatography over silica gel with hexane:ethylacetate (4:1/v:v) give a yellow oil of (E)-5-[3-(4-Fluoro-phenyl)-1-isopropyl-1H-indol-2-yl]-3-oxo-pent-4-enoic acid ethyl ester. MS: 393.46 j. (E)-(S)-5-[3-(4-Fluoro-phenyl)-1-isopropyl-1H-indol-2-yl]-3-hydroxy-pent-4-enoic acid ethyl ester A solution of (E)-5-[3-(4-Fluoro-phenyl)-1-isopropyl-1H-indol-2-yl]-3-oxo-pent-4-enoic acid ethyl ester (2.0 g, 5.08 mmol), $Ru[(1R,2R)-p-TsNCH(C_6H_5)CH(C_6H_5)NH_2]Cl(\eta^6-p\text{-cymene})$ (12.8 mg, 0.025 mmol) and a mixture of HCOOH (1.40 g, 30.5 mmol)/$NEt_3$ (1.23 g, 12.2 mmol) is heated in DMF (8.0 ml) at 50° C. for 21 h. After that the solution is diluted with MTBE (5 ml) and neutralised with $NaHCO_3$ (4 ml). Standard aquous work-up with NaCl solution and extraction with MTBE and removel of the solvent give the crude product. Chromatography on silica gel using a 4:1 hexane-MTBE mixture as eluent to afford of (E)-(S)-5-[3-(4-Fluoro-phenyl)-1-isopropyl-1H-indol-2-yl]-3-hydroxy-pent-4-enoic acid ethyl ester. MS: 395.48 k. (E)-(S)-7-[3-(4-Fluoro-phenyl)-1-isopropyl-1H-indol-2-yl]-5-hydroxy-3-oxo-hept-6-enoic acid tert-butyl ester To a solution of diisopropylamine (0.96 g, 9.53 mmol) in tetrahydrofuran (THF) (10 ml) at 0° C. is added n-BuLi (6.32 ml, 10.12 mmol of a 1.6 M solution in hexane) over 10 min. After 30 min the solution is cooled to −78° C. and t-butyl acetate (1.17 g, 10.12 mmol) is added over 10 min. After 30 min the resulting solution at −78° C. is transferred to a solution of (E)-(S)-5-[3-(4-Fluoro-phenyl)-1-isopropyl-1H-indol-2-yl]-3-hydroxy-pent-4-enoic acid ethyl ester (1.0 g, 2.53 mmol) in THF (12 ml) at 0° C. The solution is stirred 3 h at room temperature (RT). A $NH_4Cl$ solution (3 ml) is added. The mixture is poured into water (5 ml) and extracted with MTBE (50 ml). The combined organic extracts are dried over $Na_2SO_4$, filtered, concentrated, and the residue purified by flash chromatography (hexane/MTBE 5:1) to afford ketoester (E)-(S)-7-[2-cyclopropyl-4-(4-fluoro-phenyl)-quinolin-3-yl]-5-hydroxy-3-oxo-hept-6-enoic acid tert-butyl ester. MS: 465.57 l. (E)-(3R,5S)-7-[3-(4-Fluoro-phenyl)-1-isopropyl-1H-indol-2-yl]-3,5-dihydroxy-hept-6-enoic acid tert-butyl-ester To a solution of ketoester (E)-(S)-7-[3-(4-Fluorophenyl)-1-isopropyl-1H-indol-2-yl]-5-hydroxy-3-oxo-hept-6-enoic acid tert-butyl ester (1.0 g, 2.15 mmol) in THF (22 ml) and MeOH (4 ml) at −78° C. is added diethylmethoxyborane (2.70 ml of a 1 M solution in THF, 2.682 mmol). After 1 h $NaBH_4$ (0.163 g, 4.30 mmol) is added. After an additional 3 h at −78° C. pH 7 buffer (6 ml) is added followed by MeOH (7 ml). After 10 min a solution of MeOH (6 ml) and 30% aqu. $H_2O_2$ (6 ml) is added slowley. The cold bath is removed and the solution stirred for 1.5 h. The mixture is poured into $NaHCO_3$ (70 ml) and extracted with $CH_2Cl_2$ (3×50 ml). The organic extracts are dried over $Na_2SO_4$, filtered, and concentrated. The residue is dissolved in hot EtOAc (10 ml), filtered and stirred for 12 h at RT. After filtration diol (E)-(3R,5S)-7-[3-(4-Fluoro-phenyl)-1-isopropyl-1H-indol-2-yl]-3,5-dihydroxy-hept-6-enoic acid tert-butyl ester is obtained. MS: 467.58 m. (E)-(3S,5S)-7-[3-(4-Fluoro-phenyl)-1-isopropyl-1H-indol-2-yl]-3,5-dihydroxy-hept-6-enoic acid tert-butyl ester To a cooled (−35° C.) solution of $Me_4NHB(OAc)_3$ (1.38 g, 5.26 mmol) in MeCN/AcOH (15 ml, 1:1) is added a solution of ketoester (E)-(S)-7-[2-cyclopropyl-4-(4-fluoro-phenyl)-quinolin-3-yl]-5-hydroxy-3-oxo-hept-6-enoic acid tert-butyl ester (0.50 g, 1.07 mmol) in $CH_3CN$ (2 ml). The mixture is stirred at −35° C. for 3 h and at 0° C. for 30 min before a solution of potassium sodium tartrate (10 ml) is added. After 10 min the suspension is poured into $CH_2Cl_2$ (30 ml) and a solution of $Na_2CO_3$ (7 ml) is carefully added. The organic layer is separated and the aquous layer is extracted with $CH_2Cl_2$ (2×50 ml). The combined organic extracts are dried over $Na_2SO_4$, filtered, concentrated, and the residue is purified by flash chromatography (hexane/MTBE 1:1) or crystallization (ethylacetate=EtOAc) to afford diol (E)-(3S,5S)-7-[3-(4-Fluoro-phenyl)-1-isopropyl-1H-indol-2-yl]-3,5-dihydroxy-hept-6-enoic acid tert-butyl ester. MS:: 467.58 n. Sodium (E)-(3R,5S)-7-[3-(4-fluoro-phenyl)-1-isopropyl-1H-indol-2-yl]-3,5-dihydroxy-hept-6-enoate To 30 g of ester E)-(S)-7-[3-(4-Fluoro-phenyl)-1-isopropyl-1H-indol-2-yl]-5-hydroxy-3-oxo-hept-6-enoic acid tert-butyl ester in 150 ml of ethanol is added under stirring 63 ml of sodium hydroxide solution while maintaining the temperature below 12° C. The solution is stirred for 1 hour, the mixture is concentrated at 25 mm Hg and 45° C., then 220 ml of water are added, destination is continued to a remaining volume of 100 ml, then 280 ml of water are added and the solution is washed with a total of 450 ml of MTBE in 3 portions. The aquous layer is concentrated at 25 mm Hg and 45° C. to a volume of about 200 ml, 150 ml water are added, and the clear aquous solution is lyophylized over 3 days. MS: 433.21

What is claimed is:

1. A process for the manufacture of a compound of formula

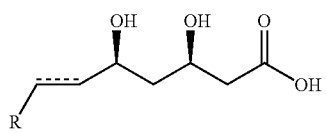
(I)

or a salt thereof or a lactone thereof, wherein the element

----- represents —CH$_2$—CH$_2$— or —CH=CH— and R represents a cyclic residue, comprising (a) reacting a compound of formula (II a)

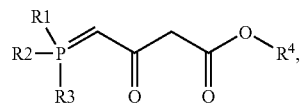
(II a)

wherein R$^1$, R$^2$ and R$^3$, independently of one another, represents phenyl that is un-substituted or substituted by one or more substituents selected from the group consisting of C$_1$–C$_7$alkyl, hydroxy, C$_1$–C$_7$alkoxy, C$_2$–C$_8$alkanoyl-oxy, halogen, nitro, cyano, and CF$_3$, and R$^4$ is an aliphatic, cycloaliphatic, araliphatic or aromatic residue;

with a compound of formula R—CH(=O) (II b) wherein R represents a cyclic residue; and (b) reducing a resulting compound of formula (II c)

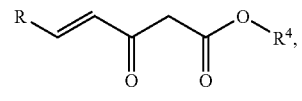
(II c)

wherein R and R$^4$ have the meanings as defined above; in the presence of a reducing agent selected from the group consisting of a compound of formulae (II d), (II d'), (II d''), (II d'''), (II d''''), (II d'''''), and (II d'''''')

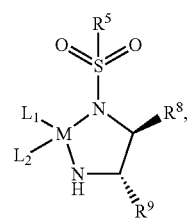
(IId)

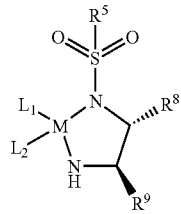
(IId')

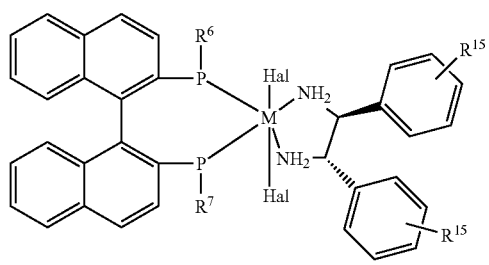
(IId'')

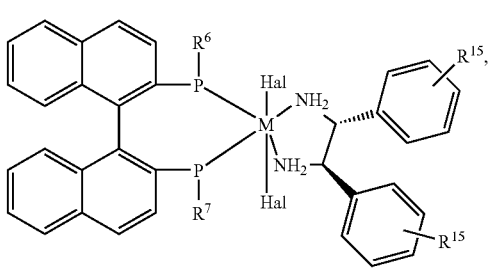
(IId''')

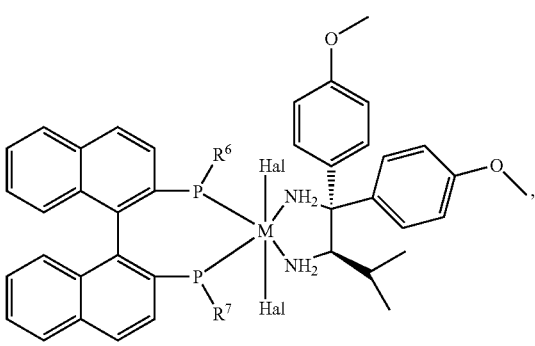
(IId'''')

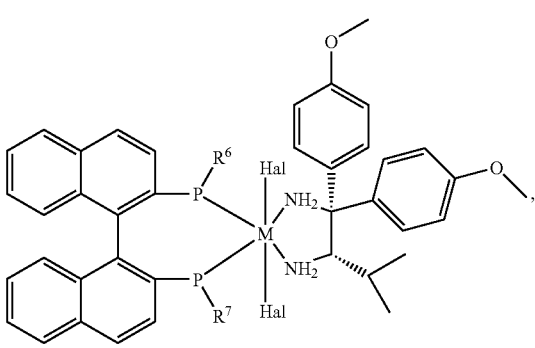
(IId''''')

-continued

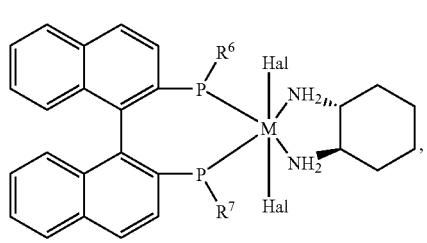
(IId'''''')

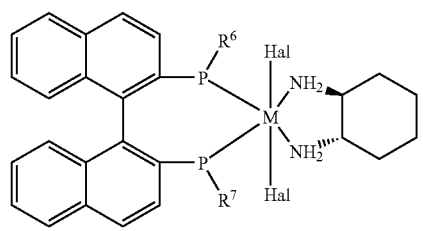
(IId''''''')

wherein
M is Ru, Rh, Ir, Fe, Co or Ni;
$L_1$ is hydrogen;
$L_2$ represents an aryl or aryl-aliphatic residue;
Hal is halogen;
$R^5$ is an aliphatic, cycloaliphatic, cycloaliphatic-aliphatic, aryl or aryl-aliphatic residue, which, in each case, may be linked to a polymer;
each of $R^6$ and $R^7$, independently, is an aliphatic, cycloaliphatic, cycloaliphatic-aliphatic, aryl or aryl-aliphatic residue;
each of $R^8$ and $R^9$ is phenyl or $R^8$ and $R^9$ form together with the carbon atom to which they are attached a cyclohexane or cyclopentane ring; and
$R^{15}$ is H, halogen, amino, nitro or $C_1$–$C_7$alkoxy;
wherein any aromatic residue of a compound of formula (IId), (IId'), (IId''), (IId'''), (IId''''), (IId'''''), (IId'''''') or (IID''''''') is unsubstituted or substituted;
wherein for compounds of formula (IId''), (IId'''), (IId''''), (IId'''''), (IId'''''') or (IID''''''') also combinations with (R)— or (S)-BINAP are possible; and
(c) condensing a resulting compound of formula (II e)

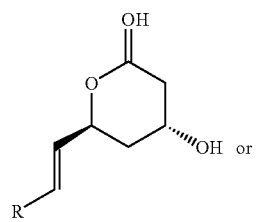
(II e)

wherein R and $R^4$ have the meanings as defined above, with a compound of formula (II f)

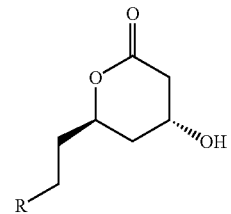
(II f)

wherein $R^{16}$ represents an aliphatic residue, and
(d) reducing a resulting compound of formula (II g)

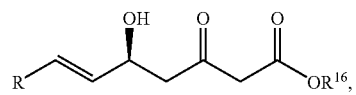
(II g)

wherein R and $R^{16}$ have the meanings as defined above, and
(e) hydrolysing a resulting compound of formula (II h)

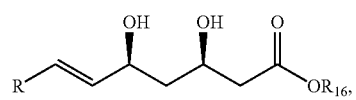
(II h)

wherein R and $R^{16}$ have the meanings as defined above, and
(f) isolating a resulting compound of formula (I) or a salt thereof;
optionally, converting a resulting free acid of formula (I) into a salt thereof or into a lactone of formula (I a) or (I b), respectively,

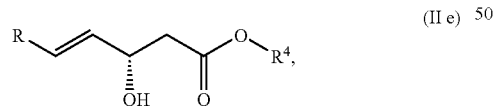

(Ia)

(Ib)

or converting a resulting compound of formula (I) wherein the element

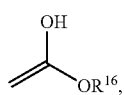

represents —CH═CH— into a compound of formula (I) wherein the element

----- represents —CH$_2$—CH$_2$—.

2. A process according to claim 1, wherein a compound of formulae (II a), (II c), (II e), (II g) and (II h) is used, wherein $R^4$ or $R^{16}$, respectively, represent $C_1$–$C_4$alkyl.

3. A process for the manufacture of a compound of formula (II e)

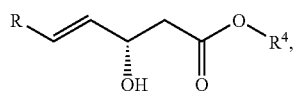 (II e)

wherein R and R⁴ have the meanings as defined in claim 1, characterized by
reducing a resulting compound of formula (II c)

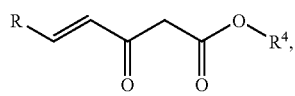 (II c)

wherein R and R⁴ have the meanings as defined in claim 1; in the presence of a reducing agent of formula

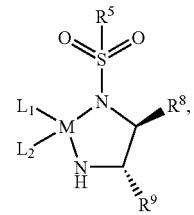 (IId)

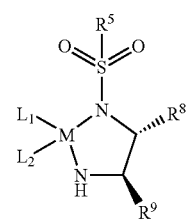 (IId')

wherein M, $L_1$, $L_2$, $R^8$ and $R^9$ are as defined in claim 1 and $R^5$ is a group of formula

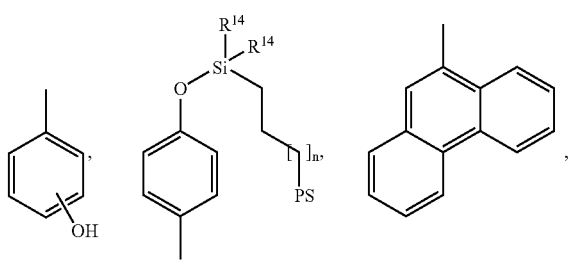

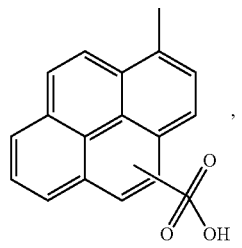, 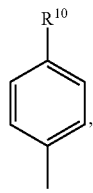,

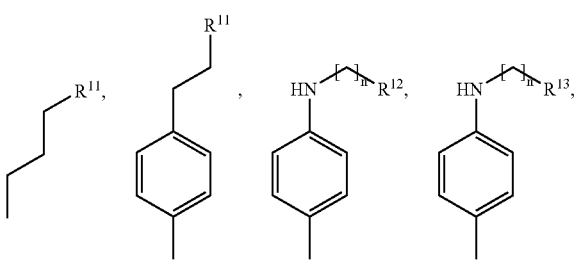

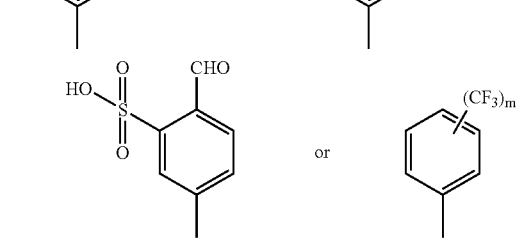

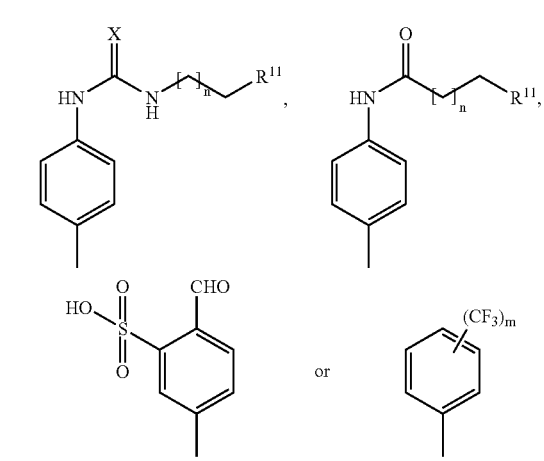

wherein
  n is 0, 1, 2, 3, 4, 5, 6 or 7;
  X is O or S;
  $R^{10}$ is polystyrol;
  $R^{11}$ is silica gel;
  $R^{12}$ is cross-linked polystyrol;
  $R^{13}$ is polyethylene-glycol;
  $R^{14}$ is $C_1$–$C_6$alkyl; and
  m is 1, 2 or 3.

* * * * *